United States Patent [19]
Arthur et al.

[11] Patent Number: 5,427,924
[45] Date of Patent: Jun. 27, 1995

[54] GENE REGULATION CASSETTES, EXPRESSION VECTORS CONTAINING THE SAME AND MICROORGANISMS TRANSFORMED WITH THE SAME

[75] Inventors: Patrick M. Arthur, Middletown, Md.; Brian C. Duckworth, Boston, Mass.

[73] Assignee: Otsuka Pharmaceutical Co., Ltd., Tokyo, Japan

[21] Appl. No.: 963,259

[22] Filed: Oct. 19, 1992

Related U.S. Application Data

[63] Continuation of Ser. No. 387,451, Jul. 31, 1989, abandoned, which is a continuation-in-part of Ser. No. 232,732, Aug. 16, 1988, abandoned.

[51] Int. Cl.⁶ ............... C12N 15/67; C12N 15/70; C12N 15/71; C12N 15/73
[52] U.S. Cl. ............... 435/69.5; 435/69.52; 435/252.3; 435/252.33; 435/320.1; 536/24.1; 935/29; 935/41; 935/47; 935/73
[58] Field of Search ............... 435/69.1, 69.5, 172.3, 435/252.3, 252.33, 320.1, 69.52; 935/29, 47, 41, 73; 536/23.1, 23.51, 24.1

[56] References Cited

FOREIGN PATENT DOCUMENTS 0138437 4/1985 European Pat. Off. .

OTHER PUBLICATIONS

Zabeau et al; EMBO J. 1: 1217 (1982).
Stewart et al; Plasmid 15: 182 (1986).
Bressan et al; Nucleic Acids Res. 15: 10056 (1987).

*Primary Examiner*—James Martinell
*Attorney, Agent, or Firm*—Sughrue, Mion, Zinn, Macpeak & Seas

[57] ABSTRACT

The present invention relates to gene regulation cassettes useful for (1) detecting the specific mRNA sequences which best enhance the translation efficiency of mRNA into protein when a specific foreign gene is adjacent thereto and (2) expressing foreign genes in procaryotic cells; expression vectors containing the gene regulation cassettes adjacent to a foreign gene such that the expression of the foreign gene is under the control of the gene regulation cassettes; and microorganisms transformed with the expression vectors. In the former gene regulation cassette, a restriction site encompasses or is adjacent to 2 base pairs 3' of the start of mRNA transcription of the lambda $P_R$ operator/promoter. This gene regulation cassette is useful for inserting and selecting sequences that generate a favorable rate of translation efficiency of the foreign gene. In the latter gene regulation cassette, a lambda $P_R$ operator/promoter is fused to a modified ribosome binding site. This gene regulation cassette is useful for obtaining a favorable rate of translation efficiency of, inter alia, the IL-1β gene and a truncated form of the M-CSF gene.

23 Claims, 4 Drawing Sheets

GENE REGULATION CASSETTES, EXPRESSION VECTORS CONTAINING THE SAME AND MICROORGANISMS TRANSFORMED WITH THE SAME

CROSS-REFERENCE TO RELATED APPLICATION

This is a continuation of application No. 07/387,451 filed 31, Jul. 1989, now abandoned, which is a continuation-in-part of application No. 07/232,732 filed 16 Aug. 1988, now abandoned.

FIELD OF THE INVENTION

The present invention relates to gene regulation cassettes useful for (1) detecting the specific mRNA sequences which best enhance the translation efficiency of mRNA into protein when a specific foreign gene is adjacent thereto and (2) expressing foreign genes in procaryotic cells; expression vectors containing the gene regulation cassettes adjacent to a foreign gene such that the expression of the foreign gene is under the control of the gene regulation cassettes; and microorganisms transformed with the expression vectors. In the former gene regulation cassette, a restriction site encompasses or is adjacent to 2 base pairs 3' of the start of mRNA transcription of the lambda $P_R$ operator/promoter. This gene regulation cassette is useful for inserting and selecting sequences that generate a favorable rate of translation efficiency of the foreign gene. In the latter gene regulation cassette, a lambda $P_R$ operator/promoter is fused to a modified ribosome binding site (hereinafter "RBS"). This gene regulation cassette is useful for obtaining a favorable rate of translation efficiency of, inter alia, the Interleukin-1β (hereinafter "IL-1β") gene, and a truncated version of the macrophage colony stimulating factor (hereinafter "M-CSF") gene.

BACKGROUND OF THE INVENTION

I. Recombinant Expression Systems

With the advent of recombinant DNA technology, it has been possible to express foreign proteins in bacteria. However, in order to make commercially practical the use of recombinant DNA technology, it is necessary to obtain a high level expression of the foreign proteins. Initial work in this area fostered the notion that a strong promoter driving expression of a foreign protein on a multicopy expression vector was the only basic requirement for efficient, high level expression (Queen, C., *J. Mol. Appl. Genet.*, 2:1-10 (1983)). Since then, further work has demonstrated that there are many other factors which can have a significant effect on the expression level of a given foreign protein. These factors can be loosely categorized as those dealing either with the genetics of the system or the physiology of the system. The genetics of the system principally involves the promoters, operators, ribosome binding sites and terminators. The physiology of the system involves the fermentation conditions. Each of these factors are discussed in detail below.

(A) Promoters and Operators

The genetic requirements for high level expression of a foreign protein start with the promoter. The promoter must be strong, i.e. it must be capable of initiating the synthesis of a large amount of mRNA. Further, the promoter must be well regulated since the expression of foreign proteins, even at low levels, may cause metabolic stress to the host, thus impeding the rapid growth of the culture to a high density (Remaut, E. et al, *Gene*, 15:81-93 (1983); Remaut, E. et al, *Nucl. Acids Res.*, 11:4677-4688 (1983); and Brosius, J., *Gene*, 27:161-172 (1984)). Hence, a well regulated promoter capable of initiating rapid mRNA synthesis at high levels upon induction has been a desired component of foreign gene expression systems.

Foreign gene expression is dependent on the interaction of RNA polymerases with the operator/promoter sequences of the foreign gene. These interactions product mRNA transcripts which contain further genetic signals, such as the RBS, that are involved in the translation of mRNA into protein. Phage lambda contains two promoters (lambda $P_R$ and lambda $P_L$) that have been used extensively in foreign gene expression systems. Each of these promoters can synthesize a high level of mRNA. These promoters are controlled by the binding of a repressor, cI, to their respective operators ($O_R1$, $O_R2$, $O_R3$, and $O_L1$, $O_L2$, $O_L3$) which blocks mRNA synthesis by inhibiting the binding of RNA polymerase. The disruption of operator-repressor binding results in derepression and the synthesis of mRNA by DNA dependent RNA polymerase.

To date, some of the most efficiently controlled promoters are obtained from mutants of phage lambda. That is, the lambda cI857 mutant contains a temperature sensitive cI repressor which is inactive at 42° C. Lambda $P_R$ or lambda $P_L$ promoters controlled by binding of the cI857 repressor to the lambda $P_R$ or lambda $P_L$ operators remain repressed at temperatures between 28° C. to 30° C. However, at 42° C., the unstable cI857 repressor no longer binds to the lambda $P_R$ or lambda $P_L$ operators, thereby causing derepression of mRNA synthesis (Isaacs, L. N. et al, *J. Mol. Biol.*, 13:963-967 (1965); and Lieb, M., *J. Mol. Biol.*, 16:149-163 (1966)).

Since there is very little detectable mRNA at 30° C. (Isaacs, L. N. et al, *J. Mol. Biol.*, 13:963-967 (1965); and Lieb, M., *J. Mol. Biol.*, 16:149-163 (1966)), foreign gene expression systems using the cI857 repressor to control the lambda $P_R$ and lambda $P_L$ promoters have been generally recognized as superior to foreign gene expression systems which employ the lac promoter (Remaut, E. et al, *Nucl. Acids Res.*, 11:4677-4688 (1983); and Bachman, K. et al, *Proc. Natl. Acad. Sci. USA*, 73:4174-4178 (1976)) or the trp promoter (Queen, C., *J. Mol. Appl. Genet.*, 2:1-10 (1983)) which initiate the synthesis of mRNA at generally lower rates/levels than do the lambda promoters.

(B) Ribosome Binding Sites

The establishment of a tightly regulated and strong promoter must be followed by an analysis of the efficiency of mRNA translation into protein. Several factors have been shown to affect the efficiency of mRNA translation into protein. More specifically, ribosomes must be able to bind efficiently at the RBS, or the Shine-Dalgarno site, on the mRNA (Steitz, J. A., R. Goldberger Ed., *Biological Regulation and Control*, Vol. 1, Plenum, New York (1978); and Shine, J. et al, *Proc. Natl. Acad. Sci. USA*, 71:1342-1346 (1974)). Then, the ribosome must be able to "read" the mRNA and translate it efficiently into protein (Roberts, T. M. et al, *Proc. Natl. Acad. Sci. USA*, 71:1342-1346 (1979); and Shepard, H. M. et al, *DNA*, 1:125-131 (1982)).

As mRNA is synthesized, it tends to fold on itself in a manner determined by the chemical affinity of the internal nucleotide bases to each other. The mRNA will thus assume a secondary structure, if not also, a tertiary structure. These structures can exhibit different forms depending on the nucleotide base composition of a given mRNA. It has been postulated that the nature of the particular mRNA structure has a profound affect on the efficiency of ribosome binding to the mRNA and mRNA translation (Iserentant, D. et al, *Gene,* 9:1-12 (1980); Kozak, M., *Microbiol. Rev.,* 47:1-45 (1983); Gheysen, D. et al, *Gene,* 17:55-63 (1982); and Hall, M. N. et al, *Nature,* 295:616-618 (1982)). The reasoning is that an unfavorable mRNA structure will "bury" the RBS in an inaccessible loop or stem, prohibiting efficient ribosome binding to the mRNA. Further, it is possible that an unstable mRNA structure may be more easily degraded before such can be translated into protein. Conversely, a very stable mRNA structure may not "unravel" easily, resulting in its inefficient "reading".

There is little information to prove or disprove the above-discussed theories because the proposed mRNA structures are predicted by computer modeling and cannot be easily experimentally confirmed. However, it is generally accepted that different primary mRNA sequences translate into protein with varying degrees of efficiency and that these differences must be related to the mRNA secondary structure (Shepard, H. M. et al, *DNA,* 1:125-131 (1982); Tessier, L. et al, *Nucl. Acids Res.,* 12:7663-7675 (1984); Whitehorn, E. et al, *Gene,* 36:375-379 (1985); and Matteucci, M. D. et al, *Nucl. Acids Res.,* 11:3113-3121 (1983)).

Moreover, attempts to express the same foreign protein using different promoters can result in different amounts of protein being synthesized from equivalent amounts of mRNA. Alternatively, a lower amount of mRNA may result in the expression of higher levels of protein. The application of this knowledge to the efficient expression of foreign proteins has been reflected in efforts to alter sequences in and around the RBS of promoter-foreign gene fusions. From these efforts, it has been found that an optimal RBS for one foreign protein is not necessarily optimal for another (Shepard, H. M. et al, *DNA,* 1:125-131 (1982); Tessier, L. et al, *Nucl. Acids Res.,* 12:7663-7675 (1984); Whitehorn, E. et al, *Gene,* 36:375-379 (1985); and Matteucci, M. D. et al, *Nucl. Acids Res.,* 11:3113-3121 (1983)).

Terminators

Another important genetic control element in foreign gene expression systems is the mRNA transcription terminator (Rosenberg, M. et al, *Ann. Rev. Genet.,* 13:319-353 (1979)). This element is composed of a recognizable mRNA sequence which signals, to the DNA polymerase, the end of mRNA synthesis as it is transcribed from a DNA sequence. The terminator sequences form secondary structures and are believed to also confer stability to the mRNA thereby preventing its degradation. As with the sequences of the RBS, the sequences of the foreign gene, when used in conjunction with any bacterial terminator, may produce a structure that, though terminating transcription efficiently, may also lack overall stability. These unstable transcripts may degrade before they can be translated to protein. Thus, experiments in which sequences in the non-translated mRNA are varied have demonstrated their significance in the level of expression of a foreign protein (Mory, Y. et al, *DNA,* 3:94 (1984)). Further, failure to terminate mRNA transcription results in the continuous synthesis or "read through", which can interfere with other expression vector functions and cause expression vector instability (Stueber, D. et al, *Embo J.,* 1:1399-1404 (1982)).

(D) Other Genetic Control Elements

The use of a highly regulated and strong promoter, an efficient RBS, and a strong terminator in foreign gene expression systems is of utmost importance. However, other genetic control elements can be introduced. These may include those which maintain or regulate control over expression vector copy number in efforts to increase expression levels, i.e., wherein an inducible promoter controls expression vector replication and thus host expression vector levels (Yarranton, G. T. et al, *Gene,* 28:293-300 (1984)). Still another approach dealing with translation efficiency involves changing the DNA sequences of the foreign genes to reflect the codon bias preferred by the host cell, such as *E. coli.* This manipulation, which maintains the amino acid integrity of the foreign gene, may further increase the translation efficiency of some foreign genes (Shaper, E., *J. Mol. Biol.,* 188:555-564 (1986); Luck, D. et al, *DNA 5,* 1:21-28 (1986); and Robinson, M. et al, *Nuc. Acids Res.,* 1217:6663-6671 (1984)).

(E) Fermentation

The physiological requirements for high level expression of foreign proteins start with the media. The media contains varying concentrations of the basic nutritional components such as carbon, nitrogen, salts, vitamins and essential minerals. Other conditions, such as the amount of agitation, aeration, pressure and the nutrient feed regimen, are also important. Further, the pH is maintained at the desired level by the addition of acid or base reagents as needed. Selection of the bacterial strain itself will dictate some of the parameters for these factors. Commercial production strains are ideally capable of reaching high cell densities in media containing only minimum requirements for growth. Strains can also be selected for their ability to produce large, stable quantities of given products. For example, they may lack the proteases that another strain uses to degrade the foreign protein (Gottesman, S. M. et al, *Cell,* 24:225-233 (1981)).

Using this basic model, an actual fermentation regimen for a given production strain can be established. Generally, seed cultures are grown and then inoculated into a fermenter at a predetermined dilution. The vessel contains a medium containing the minimum growth requirements. The culture is allowed to grow and the metabolic parameters monitored. As the culture uses its carbon source (e.g., glucose), additional amounts thereof are added such that a steady growth rate is maintained as measured by the increase in cell density over the course of time. When the culture has reached a maximum density, expression of the foreign protein is induced and the fermentation allowed to continue until the product accumulation is optimum. The vessel contents are then centrifuged to recover the cells. Next, the cells are lysed and product purification is carried out.

II. Fusion Promoters

Several fusion promoters have been employed in the art in order to enhance the efficiency of the rate of translation of foreign genes. Prominent examples thereof include the tac promoter which results from the fusion of the trp promoter and lac UV5 promoter, wherein the DNA sequences 5' to position −20 with respect to the transcriptional start site are derived from the trp promoter and the DNA sequences 3' to position −20 with respect to the transcriptional start site are derived from the lac UV5 promoter (DeBoer, H. A. et al, *Proc. Natl. Acad. Sci. USA*, 80:21-25 (1983)); the $O_L/P_R$ promoter which results from the fusion of the lambda $O_L$ operators to the lambda $P_R$ promoter at a common HincII site located in their respective −35 regions. The results promoter comprises the operator region of lambda $O_L$, including the $O_L$ −35 region, followed by the lambda $P_R$ promoter sequences starting at the lambda $P_R$ −35 region and proceeding downstream through its −10 region, continuing through the mRNA initiation site and including the lambda $P_R$ RBS (U.S. patent application Ser. No. 534,982, filed Sep. 23, 1983). This promoter is activated by raising the culture temperature. Repression at 30° C. is maintained by the lambda cI857 repressor binding to the lambda $O_L2$ and $O_L3$ repressor sites in the lambda $O_L$ operator. Raising the temperature to 42° C. inactivates the lambda repressor (Isaacs, L. N. et al, *J. Mol. Biol.*, 13:963-967 (1965)), allowing binding of RNA polymerase and mRNA synthesis (U.S. patent application Ser. No. 534,982, filed Sep. 23, 1983); and the let promoter which results from the fusion of the lambda $P_L$ operator to a portion of the trp promoter, wherein the trp promoter extending 5' from the mRNA initiation site, including the trp operator and the trp −35 region, is fused to the lambda $P_L$ operator using the HincII site located in the −35 region of the lambda $P_L$ operator (Nishi, T. et al, *Gene*, 44: 29-36 (1986)).

The tac promoter has been shown to direct expression of some genes, such as human growth hormone and galactokinase, at reasonable levels in shake flasks (DeBoer, H. A. et al, *Proc. Natl. Acad. Sci. USA*, 80:21-25 (1983)). However, the use of the tac promoter is limiting in that it cannot be completely repressed unless it is used in a strain which over produces the lac repressor. This solution disadvantageously results in a strain which does not allow full induction of the tac promoter due to the high levels of lac repressor present (Remaut, E. et al, *Gene*, 15:81-93 (1981); and Backman, K. et al, *Proc. Natl. Acad. Sci. USA*, 73:4174-4178 (1976)). The problems of regulating the tac promoter can thus be a serious disadvantage when the expression of a foreign gene has a toxic effect on cell growth, as in the case of human proinsulin and DNA polymerase I (Brosius, J., *Gene*, 27:161-172 (1984); Remaut, E. et al, *Nucl. Acids Res.*, 11:4677-4688 (1983); Hallwell, R. A. et al, *Gene*, 9:27-47 (1980); Tacon, W. et al, *Mol. Gen. Genet.*, 177:427-438 (1980); Queen, C., *J. Mol. Appl. Genet.*, 2:1-10 (1983); Remaut, E. et al, *Gene*, 15:81-93 (1981); and Kelly, W. S. et al, *Proc. Natl. Acad. Sci. USA*, 74:5632-5636 (1977)). Further, the RBS is not always a good match for every foreign gene sequence and thus can result in poor translation efficiency of some foreign genes.

The $O_L/P_R$ promoter is an improvement over the tac promoter in that it allows for much tighter regulation of expression. That is, it can repress the expression of foreign genes such that the presence of their mRNA is almost undetectable prior to induction. Although this promoter is well regulated, it does not have an RBS that will be compatible with all foreign genes. This results in poor translation efficiency of some foreign genes.

The let promoter is designed to elevate the transcription rate of the trp promoter by the use of "upstream A-T rich" regions. By using A-T rich regions from the lambda $P_L$ promoter, variable synthesis rates of recombinant human gamma-interferon in *E. coli* are observed. It is not clear whether the tight regulation normally obtained from lambda control regions is maintained with this fusion promoter. In any event, the RBS obtained, although acceptable for human gamma-interferon, may not be optimal for other foreign genes, thus limiting the use of this fusion promoter.

II. Interleukin-1β and Macrophage Colony Stimulating Factor

It has been desired in the art to obtain a well regulated promoter capable of synthesizing a high level of mRNA. Further, it has been desired in the art that this mRNA be translated efficiently when sequences of IL-1β or M-CSF are 3' to the promoter.

The tac promoter is not advantages for this purpose because, although it is capable of synthesizing high levels of mRNA, is not well regulated and the inducer is an exogenous chemical, i.e. isopropyl-β-D-thiogalactoside-IPTG.

Furthermore, the $O_L/P_R$ promoter is not advantageous for this purpose because, although it is well regulated and capable of high level mRNA synthesis, it does not carry an RBS compatible with IL-1β or M-CSF sequences.

In addition, although the let promoter may provide tight regulation, it is not adequate for this purpose because sequence changes were made in a region where they might affect transcriptional activity. As a result, there may be background transcription prior to induction. Furthermore, the let promoter also contains a trp operator site which may interfere with efficient promoter induction by slowing mRNA polymerase activity.

SUMMARY OF THE INVENTION

Accordingly, an object of the present invention is to provide a gene regulation cassette useful for detecting the specific mRNA sequences which best enhance the translation efficiency of mRNA into protein when a specific foreign gene is adjacent thereto.

An additional object of the present invention is to provide a gene regulation cassette useful for the expression of foreign genes in procaryotic cells.

A further object of the present invention is to provide a gene regulation cassette useful for the expression of IL-1β in procaryotic cells.

Still another object of the present invention is to provide a gene regulation cassette useful for the expression of M-CSF in procaryotic cells.

Another object of the present invention is to provide expression vectors containing the gene regulation cassettes adjacent to a foreign gene.

Still another object of the present invention is to provide microorganisms transformed with the expression vectors.

These and other objects of the present invention will be apparent from the detailed description of the invention provided hereinafter.

The above-described objects of the present invention have been met in one embodiment by a gene regulation cassette comprising the lambda $P_R$ operator/promoter, 2 base pairs 3' of the start of transcription of the lambda $P_R$ operator/promoter and a restriction site encompassing or adjacent to said 2 base pairs.

The above-described objects of the present invention have been met in another embodiment by a gene regulation cassette comprising the lambda $P_R$ operator/promoter fused to the 5' untranslated sequences of the tryptophan leader including a ribosome binding site.

In another embodiment of the present invention, the above-described objects have been met by expression vectors wherein a series of different 5' untranslated leader sequences, containing an RBS, have been inserted into the gene regulation cassettes to give rise to novel fusions of promoter/leader sequences.

In still another embodiment of the present invention, the above-described objects have been met by expression vectors comprising the gene regulation cassettes adjacent to a foreign gene such that the expression of the foreign gene is controlled by the gene regulation cassettes.

In yet another embodiment of the present invention, the above-described objects have been met by microorganisms transformed with the expression vectors.

DETAILED DESCRIPTION OF THE INVENTION

Figure 1:
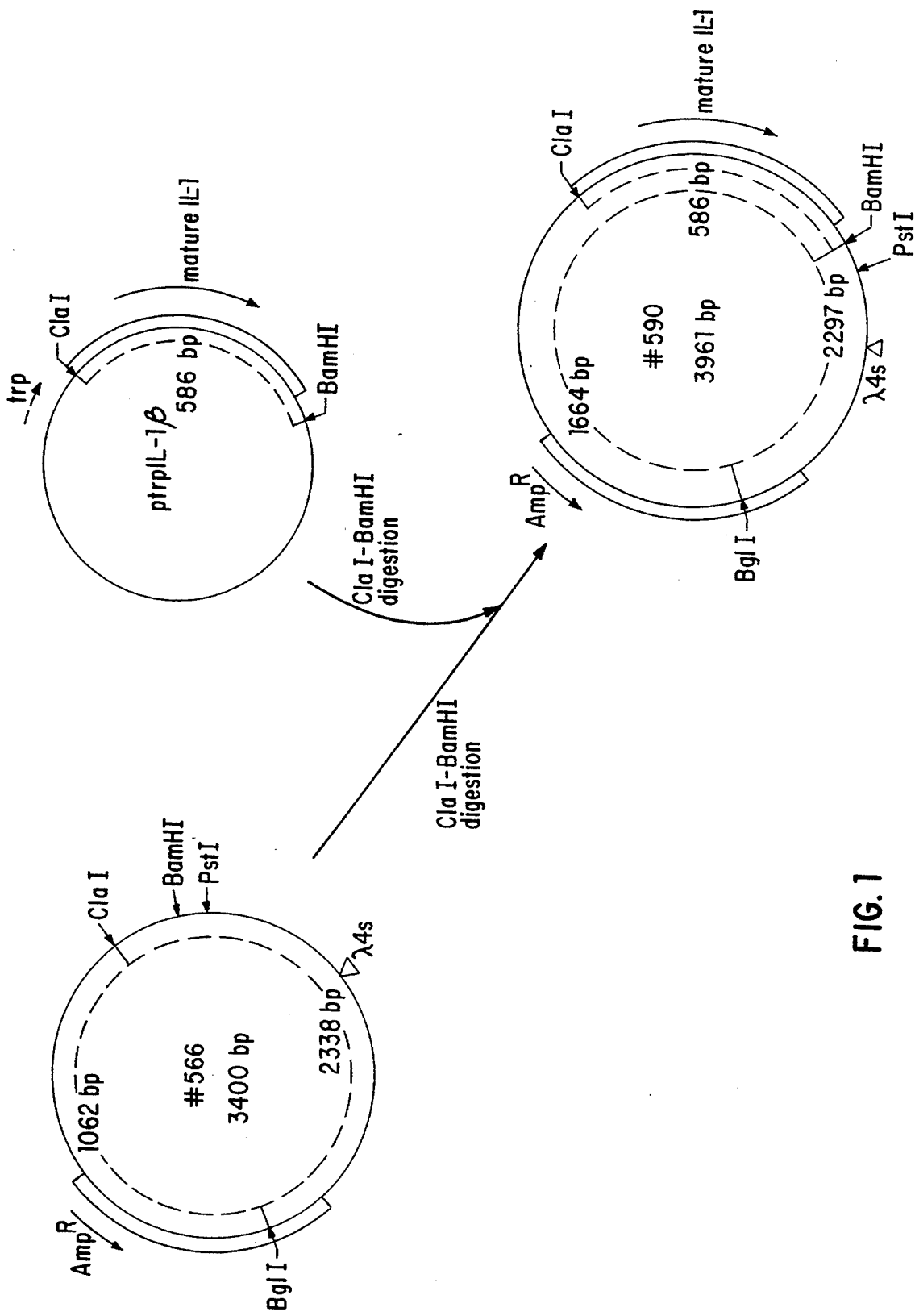
FIG. 1 schematically illustrates the synthesis of plasmid #590 from plasmid #566 and ptrpIL-1$\beta$.

As discussed above, the above-described objects of the present invention have been met in one embodiment by a gene regulation cassette comprising the lambda $P_R$ operator/promoter, 2 base pairs 3' of the start of transcription of the lambda $P_R$ operator/promoter and a restriction site encompassing or adjacent to said 2 base pairs.

Using this gene regulation cassette, it is possible to insert, at the restriction site, the 5' untranslated RBS-containing sequences that, together with the particular foreign gene sequences, give rise to the most efficient translation efficiency of mRNA.

The particular restriction site is not critical to the present invention as long as it is a restriction site which is found only once in the vector in which the gene regulation cassette is inserted. The restriction sites encompassing the 2 base pairs 3' of the start of transcription of the lambda $P_R$ promoter, i.e., "AT", include any restriction site recognized by a restriction endonuclease where "AT" are the first two bases of the recognition sequence or where "T" is the first base of the recognition sequence. Examples of such restriction sites include ClaI, AseI, BspHI, BspMII, BstBI, DraI, FspI, MseI, NruI, NsiI, and XbaI sites. Examples of restriction sites which can be adjacent to the 2 base pairs 3' of the start of transcription of the lambda $P_R$ promoter include PvuII, XbaI, XhoI and MluI sites.

If desired, two restriction sites can be used adjacent to each other so as to provide a method for directional insertion of an oligonucleotide splint.

Currently, although some promoters are well regulated, they do not provide a universally efficient RBS (Shepard, H. M. et al, *DNA*, 1: 125–131 (1982); Tessier, L. et al, *Nucl. Acids Res.*, 12:7663–7675 (1984); Whitehorn, E. et al, *Gene*, 36:375–379 (1985); and Matteucci, M. D. et al, *Nucl. Acids Res.*, 11:3113–3121 (1983)). It is thus advantageous to obtain a gene regulation cassette in which new 5' untranslated RBS-containing sequences can be easily inserted between the transcriptional control elements and the foreign gene of interest.

As demonstrated in the Examples provided hereinafter, the above-described gene regulation cassette, which is contained in plasmid #595 or plasmid #660, has been used in the present invention to effectively select 5' untranslated RBS-containing sequences for the efficient expression of IL-1$\beta$ and a truncated form of M-CSF. The heretofore known promoters consistently failed to give satisfactory IL-1$\beta$ expression levels and M-CSF expression levels, either due to a lack of control or inefficient translation of mRNA. That is, the trp promoter is not well regulated and produces a relatively low level of mRNA, although such is efficiently translated for IL-1$\beta$ and M-CSF. In the case of M-CSF, more efficient regulation of the gene's expression is essential because the accumulation of even low levels of protein is deleterious to the host cell, i.e., arrested cell growth rates arise which prohibits the production of high levels of M-CSF in the large scale production thereof. Furthermore, the lambda $P_R$ promoter, while well regulated and producing high levels of mRNA, does not translate IL-1$\beta$ and M-CSF mRNA well.

The native sequence of the lambda $P_R$ operator/promoter employed in the present invention is well known in the art (Queen, C., *J. Mol. Appl. Genet.*, 2:1–10 (1983); and Isaacs, L. N. et al, *J. Mol. Biol.* 13:963–967 (1965)). The native sequence, including the 5' untranslated RBS-containing sequences, is as follows:

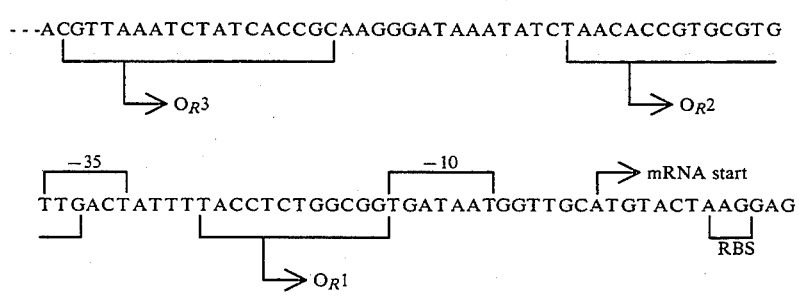

GTTGTATG---
     └── start of the lambda Cro gene

In plasmid pCQV₂ (Queen, C., *J. Mol. Appl. Genet.*, 2:1-10 (1983)), employed in the Examples provided hereinafter, the above sequence is modified at the 3' end by incorporating a BamHI site as shown below:

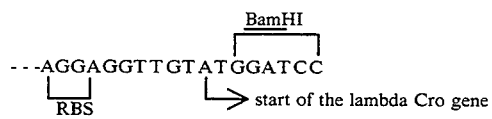

```
              BamHI
              ┌──────┐
---AGGAGGTTGTATGGATCC
   └──┘       └─> start of the lambda Cro gene
   RBS
```

Foreign genes can be inserted at the BamHI site. Further, the ATG codon 5' to the BamHI site can be used as an initiating codon.

In the Examples provided hereinafter, this region was modified to create a ClaI site as shown below:

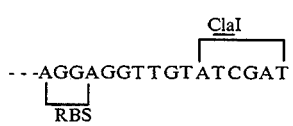

```
              ClaI
              ┌────┐
---AGGAGGTTGTATCGAT
   └──┘
   RBS
```

Foreign genes carrying their own ATG initiating codon can be added at the ClaI site, such as in plasmid #591 and plasmid #660, described in detail below.

As discussed above, in this embodiment of the present invention, there is a ClaI site encompassing 2 base pairs 3' of the mRNA transcription start site of the lambda P$_R$ operator/promoter as shown below:

slated RBS-containing sequences between transcriptional regulation units and a foreign gene of interest in order to find those sequences which provide a good match for translational efficiency of the foreign gene. A series of these 5' untranslated RBS-containing sequences can be synthesized and ligated into the ClaI site of plasmid #595 and plasmid #660, which contain the foreign gene and initiating ATG codon 3' to the ClaI site. The resulting population of recombinant plasmids will contain a series of permutations which will translate mRNA into protein with varying degrees of efficiency. Those recombinant plasmids of interest can be selected by assays directed to the detection of the foreign protein as described in the Examples provided hereinafter.

In another embodiment, the present invention relates to a gene regulation cassette comprising the lambda P$_R$ operator/promoter fused to the 5' untranslated sequences of the tryptophan leader including a ribosome binding site.

It has been found in the present invention that the fusion of the lambda P$_R$ operator/promoter to the trp RBS in plasmid #599 created a system which is well regulated, synthesizes high levels of IL-1β mRNA, and translates said mRNA to IL-1β protein efficiently.

In still another embodiment, the present invention relates to expression vectors comprising the gene regulation cassettes adjacent to a foreign gene such that the expression of the foreign gene is controlled by the gene regulation cassette.

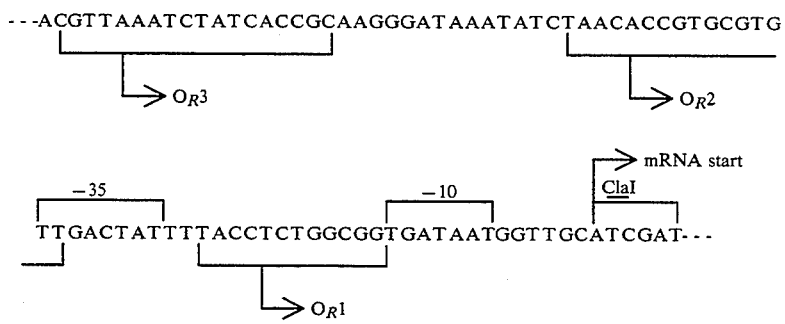

```
---ACGTTAAATCTATCACCGCAAGGGATAAATATCTAACACCGTGCGTG
      └──────┘                  └──────┘
          └─> O_R3                  └─> O_R2

-35              -10           ┌─> mRNA start
   ┌──────┐        ┌──────┐         │ ClaI
                                    ┌────┐
TTGACTATTTTACCTCTGGCGGTGATAATGGTTGCATCGAT---
└──┘        └──────────┘
         └─> O_R1
```

This gene regulation cassette is present in plasmid #595 and plasmid #660, described in detail below, and can be used to insert 5' untranslated RBS-containing sequences 5' of a foreign gene inserted 3' of the ClaI site and containing an ATG initiating codon. Selection can then be made for those sequences which optimize translation efficiency of the foreign gene.

The advantages of the gene regulation cassette in plasmid #595 and plasmid #660 are that an investigator can quickly and efficiently test a variety of 5' untran- In an example of this embodiment of the present invention, sequences derived from the trp leader were inserted at the ClaI site of plasmid #595. The sequence of the trp promoter, operator and leader are well known in the art (Hawley, D. K. et al, *Nuc. Acid Res.*, 11:2237-2255 (1983)) and is as follows:

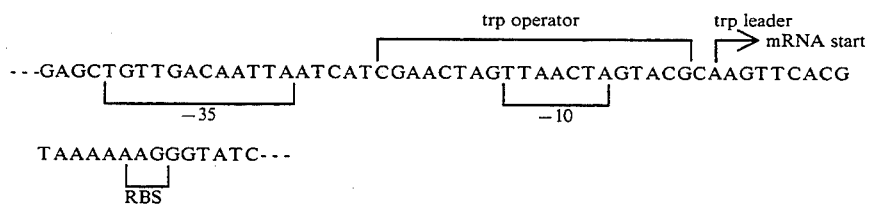

```
                        trp operator        trp leader
                    ┌──────────────────┐    ┌─> mRNA start
---GAGCTGTTGACAATTAATCATCGAACTAGTTAACTAGTACGCAAGTTCACG
          └────┘                       └──┘
           -35                          -10

TAAAAAGGGTATC---
└──────────┘
    RBS
```

The relevant sequence employed in the present invention was modified by deleting one G in the trp RBS and is as follows:

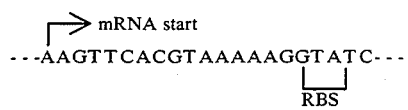
```
---AAGTTCACGTAAAAGGTATC---
                 └─RBS─┘
```
(mRNA start arrow above CGT)

When annealed with its complementary strand, the CG overhangs required for insertion into the ClaI site of plasmid #595 are provided so as to obtain plasmid #599 as shown below:

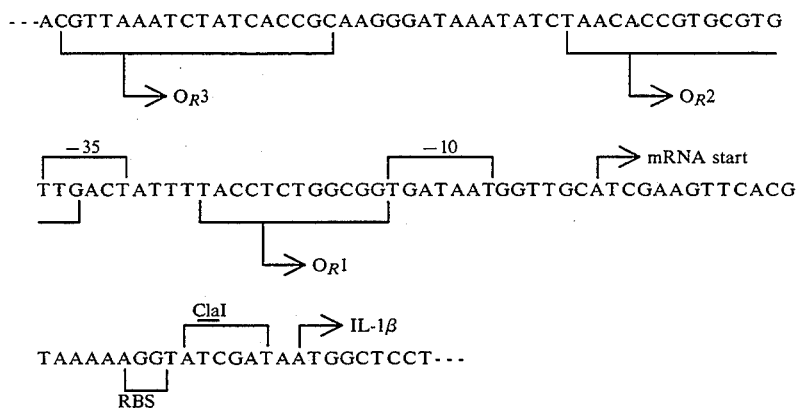

```
---ACGTTAAATCTATCACCGCAAGGGATAAATATCTAACACCGTGCGTG
         └─→ O_R3 ─┘                    └─→ O_R2 ─┘

-35              -10           ┌─→ mRNA start
TTGACTATTTTACCTCTGGCGGTGATAATGGTTGCATCGAAGTTCACG
                      └─→ O_R1 ─┘

ClaI        ┌─→ IL-1β
TAAAAAGGTATCGATAATGGCTCCT---
 └─RBS─┘
```

In this embodiment of the present invention, the lambda $P_R$/trp fusion promoter incorporates preferred changes which give rise to efficient translation of IL-1β. More specifically, the 5' end of the mRNA does not start with wild type trp sequences AAGTTCA, but rather with those from the lambda $P_R$ promoter before continuing with the trp leader sequences ATCGAAG. Furthermore, one G has been removed from the RBS site.

The 5' untranslated RBS-containing promoter employed in the present invention is not limiting. For efficient IL-1β mRNA translation, there may exist other possibilities. For other foreign genes, there are undoubtedly many possibilities. These can be synthesized from a list of known bacterial promoters (Harley, C. B. et al, *Nuc. Acid Res.*, 15:2343–2361 (1987); and Gold, L. et al, *Ann. Rev. Microbiol.*, 35:365–403 (1981)).

In another embodiment of the present invention, the gene regulation cassette of plasmid #595 was used to select 5' untranslated leader sequences for efficient translation of truncated M-CSF mRNA transcripts to protein. This was accomplished by inserting the truncated M-CSF sequences into plasmid #595 in place of the IL-1β sequences, thus creating plasmid #660. As an example, the insertion of RBS #I (see Table 1) resulted in the following sequence:

660 in nine separate ligations to give rise to plasmids #691–699, respectively. These novel plasmids were then tested for efficient truncated M-CSF production and the best plasmids were selected for further analysis.

The particular foreign gene employed in the expression vector is not critical to the present invention. Examples of such foreign genes include IL-1β or M-CSF, and analogs thereof in which amino acids have been replaced to elicit increased stabilities, activities or decreased toxicities (Auron, P. E. et al *Proc. Natl. Acad. Sci. USA*, 81:7907–7911 (1984)). Other examples of foreign genes, either procaryotic or eucaryotic, that can be inserted include all those whose expression result in a protein of scientific or commercial interest, such as enzymes, growth response modifiers and hormones.

The particular terminator employed in the present invention is not critical thereto. Examples of such terminators which are well known in the art include the lambda 4s terminator (also known as "lambda toop") (Rosenberg, M. et al, *Proc. Natl. Acad. Sci. USA*, 73:717–721 (1976)); or the bacterial rrnD (Duester, G. L. et al, *Nuc. Acids Res.*, 83793–3807 (1980)), rrnF or rrnG (Sekiya, T. et al, *Nuc. Acids Res.*, 8:3809–3827 (1980)), or rrnC terminators (Young, R. A. *J. Biol. Chem.*, 254:12725–12731 (1979)). The preferred terminator employed in the present invention is the lambda 4s terminator.

The particular vector from which the expression vector of the present invention is derived is not critical thereto. Examples of such vectors include pBR322, and its derivatives, a pUC vector, and pBR327 or derivatives thereof.

In yet another embodiment, the present invention relates to microorganisms transformed with the expression vectors.

The microorganism which is transformed in the present invention will depend upon the particular vector employed. That is, the microorganism will be one in which the vector is known to be replicated efficiently in the microorganism. Examples of the microorganisms

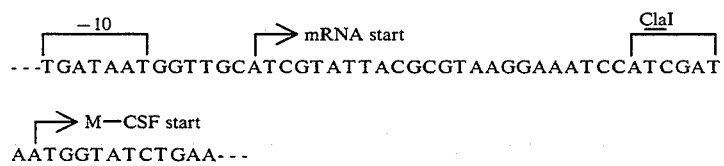
```
     -10            ┌─→ mRNA start          ClaI
---TGATAATGGTTGCATCGTATTACGCGTAAGGAAATCCATCGAT ┌─→ M—CSF start
AATGGTATCTGAA---
```

The resulting expression vector was designated plasmid #690. The remaining 5' untranslated leader sequences (RBS #II-X, see Table 1) were inserted into plasmid for pBR322 include *E. coli* K12 and mutants thereof used in recombinant DNA work, such as JM101 (ATCC No. 33876), HB101 and W3310 (ATCC No. 27325).

It is preferred in the present invention that the gene encoding the lambda cI857 repressor is also expressed by the expression vector expressing the foreign gene (Isaacs, L. N. et al, *J. Mol. Biol.*, 13:963-967 (1965); and Queen, C., *J. Mol. Appl. Genet.*, 2:1-10 (1983)). However, the lambda cI857 repressor may also be expressed on a separate expression vector which is co-transfected with the expression vector of the present invention so that the resulting microorganism contains and expresses proteins from both expression vectors (Bernard, H. J. et al, *Gene*, 5:59-76 (1979)). The cI857 gene can also be inserted into the host cell chromosome by phage transduction (Miller, J. H., *Experiments in Molecular Genetics*, Cold Spring Harbor Laboratory (1972)).

When using fermenters, the transformed microorganism is generally grown in minimum defined media using one liter volumes although larger volumes can be employed if desired. As used herein, "minimum defined media" is one in which the minimum nutrient requirements for growth are present. The basics include carbon, nitrogen, salts, vitamins, and essential minerals. Specific minerals, vitamins and amino acids vary widely depending on the strain used. The strain may further be affected by the expression of a specific gene.

The transformed microorganisms are grown in the minimum defined media generally for periods of about 6 to 12 hours, preferably about 8 to 10 hours at 28° to 32° C., preferably about 30° to 31° C. such that the cell densities have reached an O.D. of about 25 to 60 units/ml at $A_{600}$, preferably about 40 to 50 units/ml at $A_{600}$. Then, the transformed microorganisms are grown at about 40° to 42° C., preferably about 40° to 41° C. to induce foreign gene expression for about 5 to 18 hours, preferably about 10 to 16 hours. At the conclusion of this period, the cell densities have reached an O.D. of about 30 to 60 units/ml at $A_{600}$, preferably about 30 to 40 units/ml at $A_{600}$ giving rise to a yield of foreign protein in a range of from about 500 to 900 mg/liter, preferably about 500 to 750 mg/liter, depending upon the fermentation conditions. The fermentation conditions which have a marked effect on the growth rate and final cell densities include dissolved oxygen fluctuations and pH changes as well as nutrient feed regimens. Maintenance of dissolved oxygen at 20%, pH at 6.8-7.0 and constant glucose (carbon source) as needed (i.e., not more or less) can increase yields considerably.

After the end of fermentation, the cells are recovered by centrifugation. The cells are then suspended in a neutral buffer (e.g., 10 mM Tris (pH 7.0) and broken open, e.g., by passage under high (18,000 PSI) pressure in a French pressure cell. At this point, a variety of techniques can be employed. If the recombinant protein is in the form of an insoluble aggregate or stored as an "inclusion body", the protein can be separated from the total lyzate by differential centrifugation wherein the bulk of the insoluble material is recovered in a pellet and the bulk of the soluble proteins remain in the supernatant (European Patent Publication No. 218,374). Alternatively, a strong denaturant, such as 6.0M Urea, can be added, the volume increased and separation of proteins based on size or charge can proceed.

For example, materials can be passed through size exclusion filters or run over a sizing column to separate proteins based on molecular weight. The foreign protein fraction is isolated and further purified on chromatographic columns based on its specific charge. Alternatively, separations based on specific charge can be performed as a first step if the total protein concentration does not interfere with the charge separation (Regnier, F. E., *Science*, 238:319-323 (1987); U.S. Pat. No. 4,677,196; PCT Publication No. 8704726; Brewer, S. J., *Enzyme Eng. Int. Conf.*, (1986); Taylor, R. F. et al, *Bio-Expo* 86, pages 397-407 (1986); Sitrin, R. D. et al, *Am. Chem. Soc.* (1986), 192 Meet MBTD 16; Roy, S. K. et al, *Am. Chem. Soc.* (1986), 192 Meet MBTD 18; Tarnowski, D. G. *Pharm. Technol.* (1987), 11, 6, 162-64; Atkinson, T., *World Biotech Rep.*, pages 143-148 (1986)).

The following examples are provided for illustrative purposes only and are in no way intended to limit the scope of the present invention.

EXAMPLE 1

Construction of IL-1β Expression Vector

In this example, the gene regulation cassettes contain a ClaI site. However, as discussed above, other restriction sites could be employed in place of the ClaI site without departing from the spirit and scope of the present invention.

Also in this example, the IL-1β gene was inserted adjacent to the gene regulation cassettes of the present invention. However, as discussed above, and shown in Example 2 below, other foreign genes could be employed in place of the IL-1β gene without departing from the spirit and scope of the present invention.

Furthermore, in this example, the lambda 4s terminator was placed 3' to the IL-1β gene. However, as discussed above, other terminators could be employed in place of the lambda 4s terminator without departing from the spirit and scope of the present invention.

In addition, in this example, the gene encoding the lambda cI857 repressor is also expressed by the IL-1β expression vector. However, as discussed above, the lambda cI857 repressor could also have been expressed on a separate expression vector or could have been expressed from the genome of the host microorganism without departing from the spirit and scope scope of the present invention.

The IL-1β expression vector was prepared as described in detail below.

About 8.0 μg of plasmid ptrpIL-1β in 80 μl of water, was digested with 25 units of ClaI in 5.0 μl of the manufacturer's solution and 25 units of BamHI in 5.0 μl of the manufacturer's solution, in 10 μl of 10 X buffer A comprising 100 mM Tris (pH 7.5), 60 mM $MgCl_2$ and 1000 mM NaCl for 2 hours at 37° C. Plasmid ptrpIL-1β contains the IL-1β gene (Kikumoto, Y. et al, *Biochem. Biophys. Res. Commun.*, 147:315-321 (1987)) (see FIG. 1). The resulting reaction mixture was then phenol extracted, and the DNA ethanol precipitated and resuspended in 20 μl of water. The resulting digested DNA was electrophoresed on a 1.0% (w/v) agarose gel as described in Sharp, P. A. et al, *Biochem.*, 12:3055 (1973), so as to isolate a 586 base pair DNA fragment, containing sequences encoding mature IL-1β and an initiation (ATG) codon.

The 586 base pair DNA fragment was then ligated into an equal molar amount of plasmid #566 (see FIG. 1) which had previously been digested with ClaI and BamHI as described above.

Plasmid #566 is a derivative of vector pUC8 (Vieira, T. et al, *Gene*, 19:259-268 (1982)) and vector pKo-1

(ATCC No. 37126) (McKenney, et al, *Gene Amplification and Analysis*, Vol. II, 1981, pages 383-415) in which the polylinker in pUC8 was expanded by the insertion of a synthetic oligonucleotide to include more restriction endonuclease cleavage sites. Originally, pUC8 had a polylinker which included EcoRI, SmaI, BamHI, SalI and HindIII sites. In the present invention, four oligonucleotides were assembled which yielded a new polylinker additionally containing ClaI, SphI, PvuII and XbaI sites. Plasmid #566 contains the lambda 4s terminator 3' to the polylinker. Any number of commercially available vectors could have been substituted for plasmid #566 such as any of the series of pUC vectors with their own, expanded polylinkers (Boehringer Mannheim Biochemicals).

Next, *E. coli* strain HB101 were transformed with the resulting plasmids as described in the BRL protocol for transforming *E. coli* strain HB101.

Recombinant plasmids were screened by randomly selecting 16 colonies generated from the transformation. More specifically, plasmid DNA was isolated from these colonies as described by Maniatis, T. et al, *Molecular Cloning Manual*, Cold Spring Harbor Laboratory (1982). The resulting plasmid DNAs were screened by digesting each with BglI and PstI. Desired recombinant plasmids yielded 2 fragments of 1664 and 2288 base pairs while undesired vectors yielded fragments of 1054 base pairs and 2288 base pairs. In this manner, plasmid #590 was obtained (see FIG. 1).

Plasmid #590 contains the IL-1$\beta$ gene in an orientation that enables for the introduction of various gene regulation cassettes using (a) the ClaI site and (b) one of the several other restriction sites situated in the ampicillin resistance (Amp$^R$) gene (see FIG. 1). Furthermore, in plasmid #590, the lambda 4s terminator (Rosenberg, M. et al, *Proc. Natl. Acad. Sci. USA*, 73:717-721 (1976)) is situated 3' to the IL-1$\beta$ gene. This terminator functions most efficiently in the presence of rho protein, but does not require it (Rosenberg, M. et al., *Proc. Natl. Acad. Sci. USA*, 73:717-721 (1976)).

Next, about 20 to 40 $\mu$g of plasmid #590 in 40 $\mu$l of water was digested with 25 units of ClaI in 5.0 $\mu$l of the manufacturer's solution, in 10 $\mu$l of 10 X buffer B comprising 100 mM Tris (pH 7.5), 60 mM MgCl$_2$ and 500 mM NaCl, and 50 $\mu$l of water for 2 hours at 37° C. The resulting reaction mixture was phenol extracted, chloroform extracted, and the DNA ethanol precipitated and resuspended in 60 $\mu$l of water.

The 5' overhang generated by the ClaI digestion of plasmid #590 was filled in by reaction with T4 polymerase. More specifically, about 5.0 $\mu$g of ClaI-digested plasmid #590 DNA in 30 $\mu$l of water was reacted with 9.0 units of T4 DNA polymerase in 1.5 $\mu$l of the manufacturer's solution, in 10 $\mu$l of 10 X T4 buffer comprising 166 mM NH$_4$SO$_4$, 670 mM Tris (pH 8.8) and 67 mM MgCl$_2$, 10 $\mu$l of 10 mM dNTPs and 50 $\mu$l of water at 37° C. for 25 min. and then at 65° C. for 10 min. The resulting reaction mixture was phenol extracted, chloroform extracted, and the DNA ethanol precipitated and resuspended in 90 $\mu$l of water.

The resulting DNA was then digested with over 20 units of BglI in 4.0 $\mu$l of the manufacturer's solution, in 10 $\mu$l of 10 X buffer B. The resulting digested DNA was electrophoresed on a 1.0% (w/v) agarose gel as described in Sharp, P. A. et al, *Biochem.*, 12:3055 (1973) so as to isolate an about 2883 base pair fragment (see FIG. 2).

In parallel, plasmid #514 was subjected to BamHI digestion followed by filling in with T4 polymerase. Plasmid #514 is a derivative of plasmid pCQV$_2$ (Queen, C., *J. Mol. Appl. Gen.*, 2:1-10 (1983)) and contains the lambda P$_R$ operator adjacent to the lambda P$_R$ promoter. That is, in plasmid pCQV$_2$, a ClaI site 5' of the lambda cI857 gene was deleted by digesting pCQV$_2$ with ClaI and filling in the overhang with T4 polymerase was carried out in the same manner as filling in the ClaI site in plasmid #514. Then, the vector was recircularized by ligation and used to transform HB101. The resulting colonies were screened by digesting plasmids with ClaI. The plasmids which were not digested by ClaI were designated plasmid #514 because they had lost the ClaI site as desired (see FIG. 2).

More specifically, 60 $\mu$g of plasmid #514 in 39 $\mu$l of water, was digested with 200 units of BamHI in 8.0 $\mu$l of the manufacturer's solution, in 30 $\mu$l of 10 X buffer C comprising 100 mM Tris (pH 7.5), 60 mM MgCl$_2$ and 1500 mM NaCl, and 230 $\mu$l of water for 2 hours at 37° C. The resulting reaction mixture is then phenol extracted, chloroform extracted, and the DNA ethanol precipitated and resuspended in 120 $\mu$l of water (0.5 $\mu$g/$\mu$l).

The 5' overhang generated by the BamHI digestion of plasmid #514 was treated in a modified reaction with T4 polymerase. That is, the 3' to 5' nuclease activity of T4 polymerase was used to remove the first exposed 3' base "G" in the sequence generated by BamHI digestion. Addition of dTTP to the reaction insured replacement of "T" removed in the same manner since "T" is the next base encountered by the nuclease after "G". The excess of "T" in the reaction resulted in an exchange reaction and a stalling of the nuclease activity. By omitting the other dNTPS from the reaction, the 5' to 3' polymerase activity of T4 was negated, i.e., the 5' BamHI overhang was not filled in.

More specifically, 2.0 to 4.0 $\mu$g of BamHI-digested plasmid #514 in 4.0 $\mu$l of water, was reacted with 3.0 units of T4 DNA polymerase in 0.5 $\mu$l of the manufacturer's solution, in 4.0 $\mu$l of 10 X T4 buffer, 2.0 $\mu$l of 2.0 mM dTTP and 30 $\mu$l of water at 37° C. for 10 min. and then at 65° C. for 10 min., followed by the addition of 60 $\mu$l of 10 mM Tris (pH 7.5). The resulting reaction mixture was then phenol extracted, chloroform extracted, and the DNA ethanol precipitated and resuspended in 40 $\mu$l of water.

Next, the resulting DNA was subjected to mung-bean nuclease digestion in order to remove the remaining 5' overhang. More specifically, about 2.0 $\mu$g of DNA in 10 $\mu$l of water was digested with 0.3 units of mung-bean nuclease in 1.5 $\mu$l of the manufacturer's solution, in 4.0 $\mu$l of 5 X MB buffer comprising 150 mM sodium acetate (pH 4.6), 250 mM NaCl and 5.0 mM ZnCl$_2$, and 5.0 $\mu$l of water at 37° C. for 10 min. and then at 65° C. for 10 min., followed by the addition of 80 $\mu$l of TE buffer comprising 10 mM Tris (pH 7.5) and 1.0 mM EDTA. Then, 2.0 $\mu$l of 1.0M NaCl was added and the reaction mixture was phenol extracted, chloroform extracted, and the DNA ethanol precipitated and resuspended in 36 $\mu$l of TE buffer.

Thereafter, 4.0 $\mu$l of 1.0M NaCl was added and digestion was carried out with 10 units of BglI and 4.0 $\mu$l of 10 X buffer B for 2 hours at 37 °C. The resulting reaction mixture was loaded on a 1.0% (w/v) agarose gel and electrophoresed as described in Maniatis, T. et al, *Molecular Cloning Manual*, Cold Spring Harbor Laboratory (1982) so as to isolate an approximately 1689 base pair fragment (see FIG. 2).

Then, 3.0 μl of the resulting ClaI-digested-T4-polymerase-treated-BglI-digested plasmid #590 DNA and 15 μl of the resulting BamHI-digested-T4 polymerase-treated-mung-bean nuclease-digested-BglI-digested plasmid #514 DNA were ligated together with 800 units of T4 DNA ligase in 2.0 μl of the manufacturer's solution, in 2.0 μl of 10 X ligase buffer comprising 500 mM Tris (pH 7.8), 100 mM MgCl₂, 200 mM DTT and 10 mM ATP for 5 hours at 12° C. The resulting recombinant plasmids were employed to transform *E. Coli* strain HB101 as described above.

As discussed above, the above-described methods for the preparation of plasmids #590 and #514 were carried out in parallel and are illustrated schematically as follows:

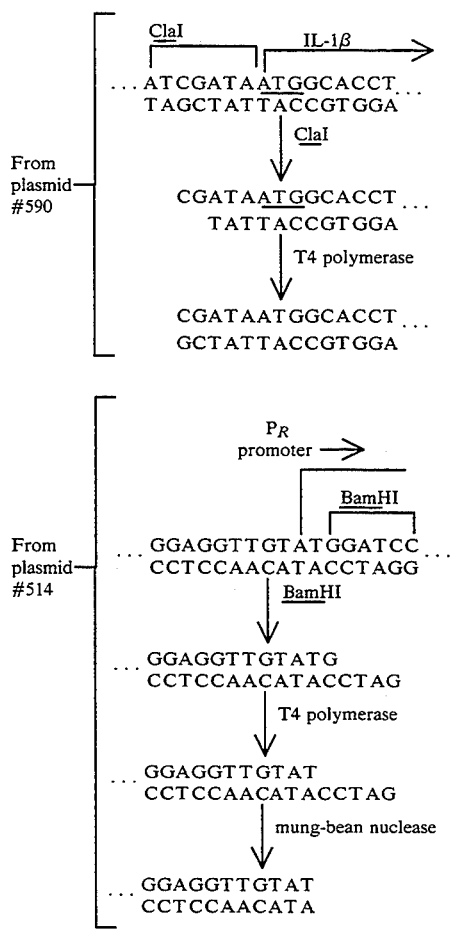

112 colonies were obtained as a result of the above-described transformation. These colonies were screened for the recreation of the ClaI site shown below.

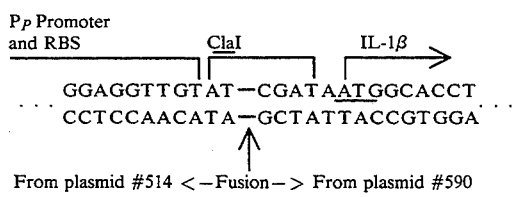

Figure 2:
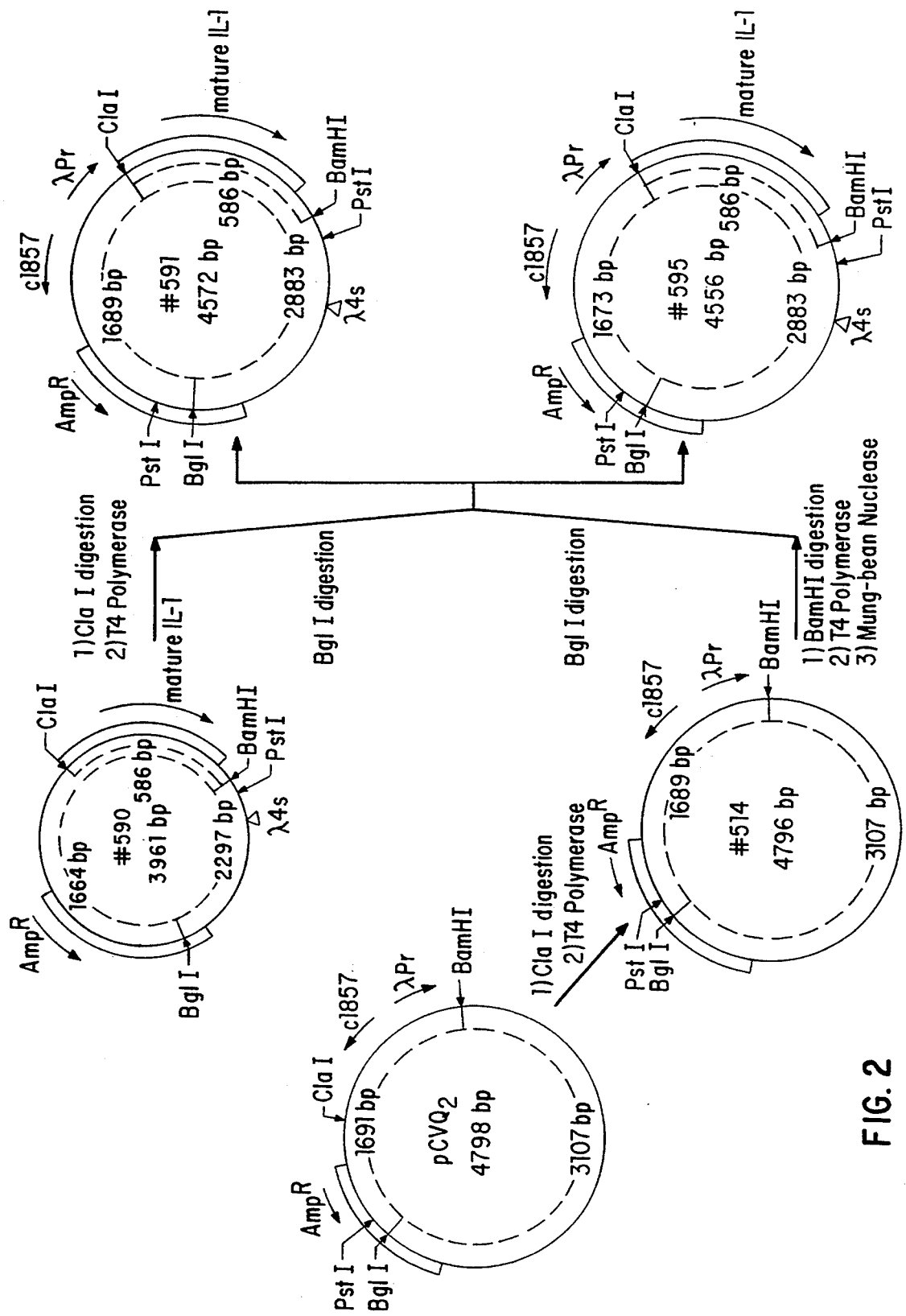
FIG. 2 schematically illustrates the synthesis of plasmid #514 from pCQV$_2$; and plasmid #591 and plasmid #595 from plasmid #590 and plasmid #514.

More specifically, plasmid preparations were made from 112 colonies and digested with ClaI. then, those plasmids that were shown to be actually cut with ClaI by analysis on 1.0% (w/v) agarose gels were sequenced and plasmid #591 was identified (see FIG. 2).

Plasmid #591 was characterized by extracting mRNA from induced and uninduced HB101 cells and probing for the presence of IL-1β mRNA. More specifically, total mRNA was prepared by resuspending 1.0 ml cell pellets, taken just prior to, and at hourly intervals following 42° C. incubation, in 200 μl of a solution comprising 25 mM Tris (pH 7.5), 10 mM EDTA, 15% (w/v) sucrose and 2.0 mg/ml lysozyme and incubation at 4° C. for 20 min. Then, 200 μl of a buffer comprising 20 mM Tris (pH 7.5), 1.0 mM EDTA and 50 mM NaCl was added along with SDS to a final concentration of 0.5% (w/v) and incubated at 65° C. for 10 min. Thereafter, the resulting solution was subjected to centrifugation at 12000×g at 23° C. for 15 min, phenol extracted, phenol-chloroform (1:1 (v/v)) extracted, chloroform extracted and precipitated with 0.3M sodium acetate and 2.5 volumes of ethanol. The resulting precipitate was washed with 70% (v/v) ethanol and dried. The dried pellet was resuspended in 100 ml of DNAse buffer comprising 20 mM Tris (pH 7.5), 1.0 mM EDTA, 10 mM MgCl₂, 10 mM CaCl₂ and 5.0 mM DTT. Next, 200 units of DNAse was added and incubated at 37° C. for 1 hour. Then, proteinase K was added to a final concentration of 50 μg/ml and SDS was added to a final concentration of 0.5% (w/v) and incubation was carried out at 37° C. for 1 hour. The resulting solution was extracted three times with phenol-chloroform (1:1 (v/v)) and precipitated with 0.3M sodium acetate and 2.5 volumes of ethanol. The resulting precipitate was washed with 70% (v/v) ethanol, dried and resuspended in 50 μl of water. The thus obtained mRNA was run over a slot blot apparatus, fixed to nitrocellulose and hybridized to an IL-1β probe as described in Maniatis, T. et al, *Molecular Cloning Manual*, Cold Spring Harbor Laboratory (1982).

Total protein extracts from induced and uninduced cells were also assayed by Western blot using an IL-1β specific antibody as described in Towbin, H. et al, *Proc. Natl. Acad. Sci. USA*, 76:4350-4354 (1979).

The results demonstrated that more IL-1β protein was being synthesized from a lower amount of mRNA in the case of ptrpIL-1β than compared to plasmid #591. That is, plasmid #591 synthesized at least 10 to 20 times more mRNA, but synthesized ½ the amount of IL-1β protein as did ptrpIL-1β. Thus, mRNA from plasmid #591 was not translated efficiently. This is believed to be due to an unfavorable mRNA secondary structure.

The colonies also contained other plasmids which had generated a ClaI site further upstream in the lambda P_R promoter region, depending on the activity of the mung-bean nuclease or the T4 polymerase on a given strand. One of the these plasmids, designated #595 (see FIG. 2), was found by DNA sequencing to have deleted all of the lambda P_R RBS sequence up to 2 base pairs 3' of the mRNA start site resulting in the following configuration:

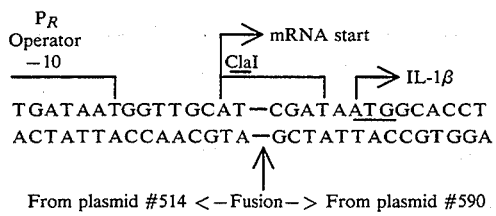

From plasmid #514 <—Fusion—> From plasmid #590

Since the secondary mRNA structure is dependent on the combined base pair composition of the 5' untranslated sequences from the leader and the 5' translated portion of the foreign gene, plasmid #595 was used to change sequences in the 5' untranslated region of the leader. Plasmid #595 is an excellent vector to select for 5' untranslated-RBS-containing sequences that match a foreign gene such that translation efficiency is enhanced because all of the regulatory elements needed for control of mRNA synthesis provided by lambda $P_R$ are located 5' of the ClaI site. The AT which defines the start of the ClaI site is also the point of mRNA synthesis initiation and can be used as such to express foreign genes inserted 3' of the ClaI site after the proper 5' untranslated, RBS-containing, leader sequences are inserted at the ClaI site.

In order to determine whether the tryptophan 5' untranslated-RBS-containing leader sequence was a good match for IL-1β synthesis, the following experimentation was carried out:

First, the synthetic oligonucleotide splint shown below was synthesized on a Gene Assembler oligonucleotide synthesizer made by Pharmacia, S. A. As illustrated below, this splint was made to closely match the trp leader sequences. Next, a 10 to 100 molar excess of splint was inserted at the ClaI site of plasmid #595. Note, the RBS in the splint contains one less "G" than the natural trp sequence and there are additional bases at the 5' end, i.e., "ATCG".

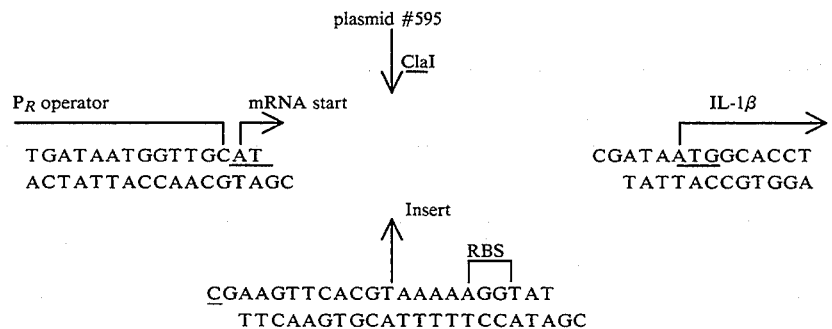

Figure 3:
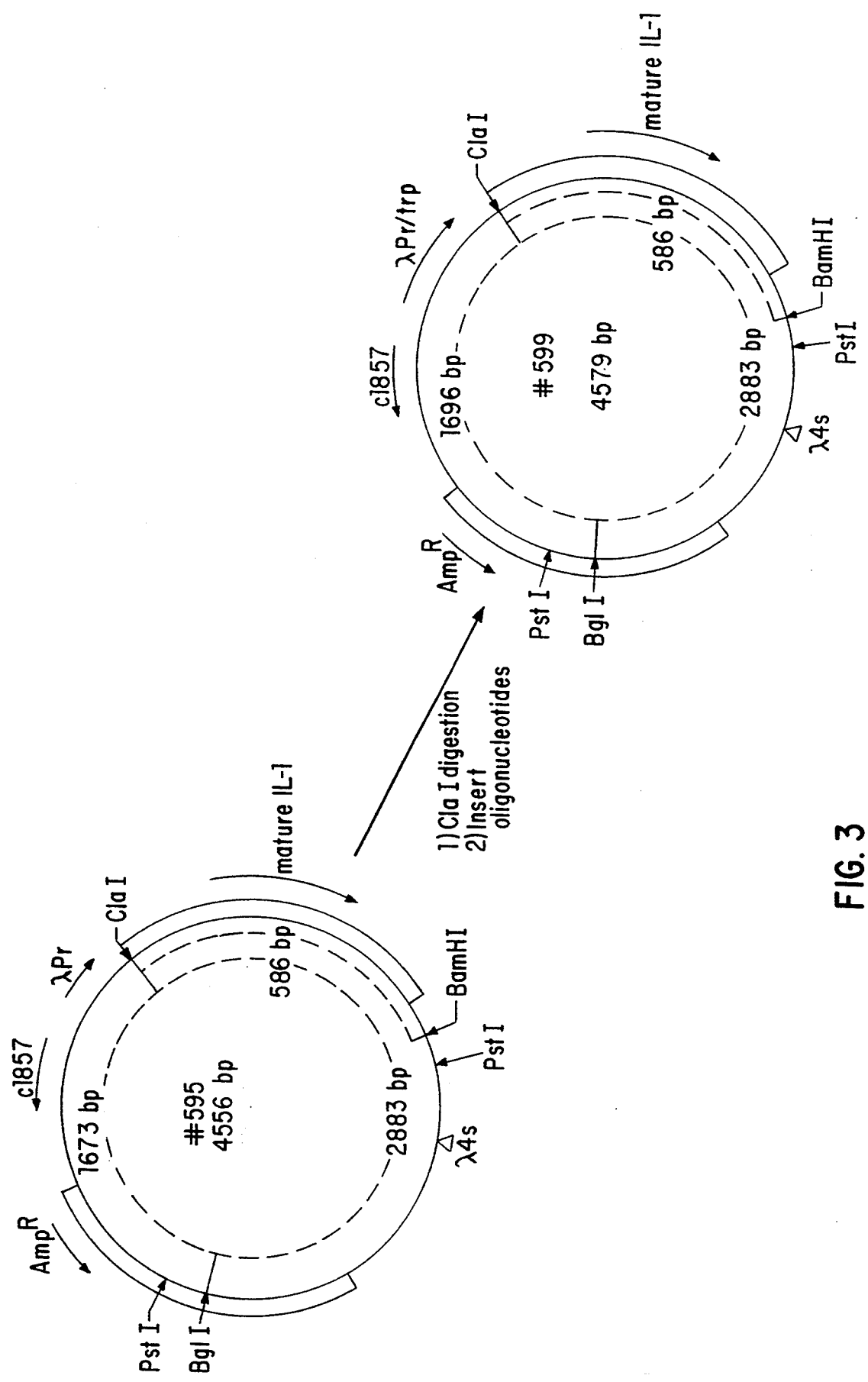
FIG. 3 schematically illustrates the synthesis of plasmid #599 from plasmid #595.

The resulting fusion promoter-RBS created, i.e., lambda $P_R$/trp, was now in an IL-1β expression vector designated plasmid #599 (see FIG. 3). Plasmid #599 was characterized as described above along with #591 and ptrpIL-1β, and found to synthesis levels of mRNA equivalent to plasmid #591. However, plasmid #599 was found to translate the mRNA at a higher efficiency, as shown by a higher level of IL-1β protein observed in plasmid #599 than in either plasmid #591 or ptrpIL-1β.

These results demonstrate that plasmid #595 is an excellent plasmid for testing new BRSs because an entire 5' untranslated sequence, including the RBS region, can be inserted at the ClaI site. Further, all of the transcriptional control elements are located 5' to the ClaI site and are unaffected by the introduced sequences.

mRNA synthesis initiates at the first "A" in the ClaI recognition sequence.

More specifically, a series of 5' untranslated-RBS-containing sequences can be synthesized and ligated simultaneously at the ClaI site in plasmid #595 or similar plasmid containing a foreign gene other than IL-1β. Using an antibody specific to the gene product of the foreign gene located 3' to the ClaI site, one can screen an entire library of colonies representing the spectrum of different leaders synthesized. This is accomplished by transforming the recombinant vectors in, e.g., E. coli and plating them on agar plates. These colonies can be induced at 42° C. and then assayed using an antibody to the foreign protein. Those colonies producing the highest level of foreign protein can then be selected.

For IL-1β, the trp-related sequences described above were found to be optimal and initial IL-1β expression tests using plasmid #599 revealed a tight regulation. That is, there was no appreciable detection of IL-1β mRNA or IL-1β mRNA levels were significantly higher than those produced by the standard trp promoter (ptrpIL-1β) and equivalent to that produced by the standard lambda $P_R$ promoter (plasmid #591). Further, with plasmid #599, the IL-1β protein level was significantly higher than with either the standard trp promoter or the lambda $P_R$ promoter.

Plasmid #599 was initially tested in E. coli strain HB101, but was eventually transformed into strain JM101 because of this strain's ability to grow more efficiently in fermenters.

Microorganisms S-#595 (HB101) and S-#599 (JM101) have been deposited at the American Type Culture Collection under ATCC Nos. 67755 and 67756, respectively.

EXAMPLE 2

Construction of a Truncated Form of M-CSF

In this example, the #595 gene regulation cassette of Example 1 was used to select a 5' untranslated leader sequence for the efficient translation of truncated M-CSF mRNA to protein.

In this example, the truncated M-CSF gene was inserted adjacent to the gene regulation cassette of the present invention.

As with Example 1, the lambda 4s terminator was used, but any other efficient transcription terminator could be used without departing from the spirit and scope of the present invention.

In addition, in this example, the gene encoding the lambda cI857 repressor is also expressed by the IL-1β expression vector. However, as discussed above, the lambda cI857 repressor could also have been expressed on a separate expression vector or could have been expressed from the genome of the host microorganism without departing from the spirit and scope of the present invention.

The truncated M-CSF expression vector was prepared as described in detail below.

About 5.0 μg of plasmid ptrpM-CSF-11-NV151 in 160 μl of water, was digested with 50 units of ClaI in 10 μl of the manufacturer's solution and 50 units of BamHI in 10 μl of the manufacturer's solution in 20 μl of 10 X buffer A (see Example 1) for 2 hours at 37° C.

Plasmid ptrpM-CSF-11-NV151 contains the truncated M-CSF gene and was obtained from pcDM-CSF-11-185 (European Patent Publication No. 261,592). More specifically, pcDM-CSF-11-185 was digested with ScaI and BamHI and the about 450 bp DNA fragment containing-M-CSF was isolated and by agarose gel electrophoresis. To the ScaI cleavage site of the resulting fragment was added the following oligonucleotide using T4 ligase.

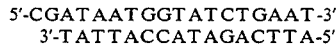

5'-CGATAATGGTATCTGAAT-3'
3'-TATTACCATAGACTTA-5'

The resulting DNA fragment, containing about 470 bp. has a ClaI cleavage site and a BamHI cleavage site at the ends thereof. Next, this DNA fragment was inserted between the ClaI and BamHI sites of plasmid pTM1 (Imanoto, F., *Taisha (Metabolism)*, 22:289 (1985)). Plasmid pTM1 contains the *E. coli* trp promoter-operator sequence. The resulting plasmid was designated ptrpM-CSF-11-NV151 (hereinafter "ptrpM-CSF").

Figure 4:
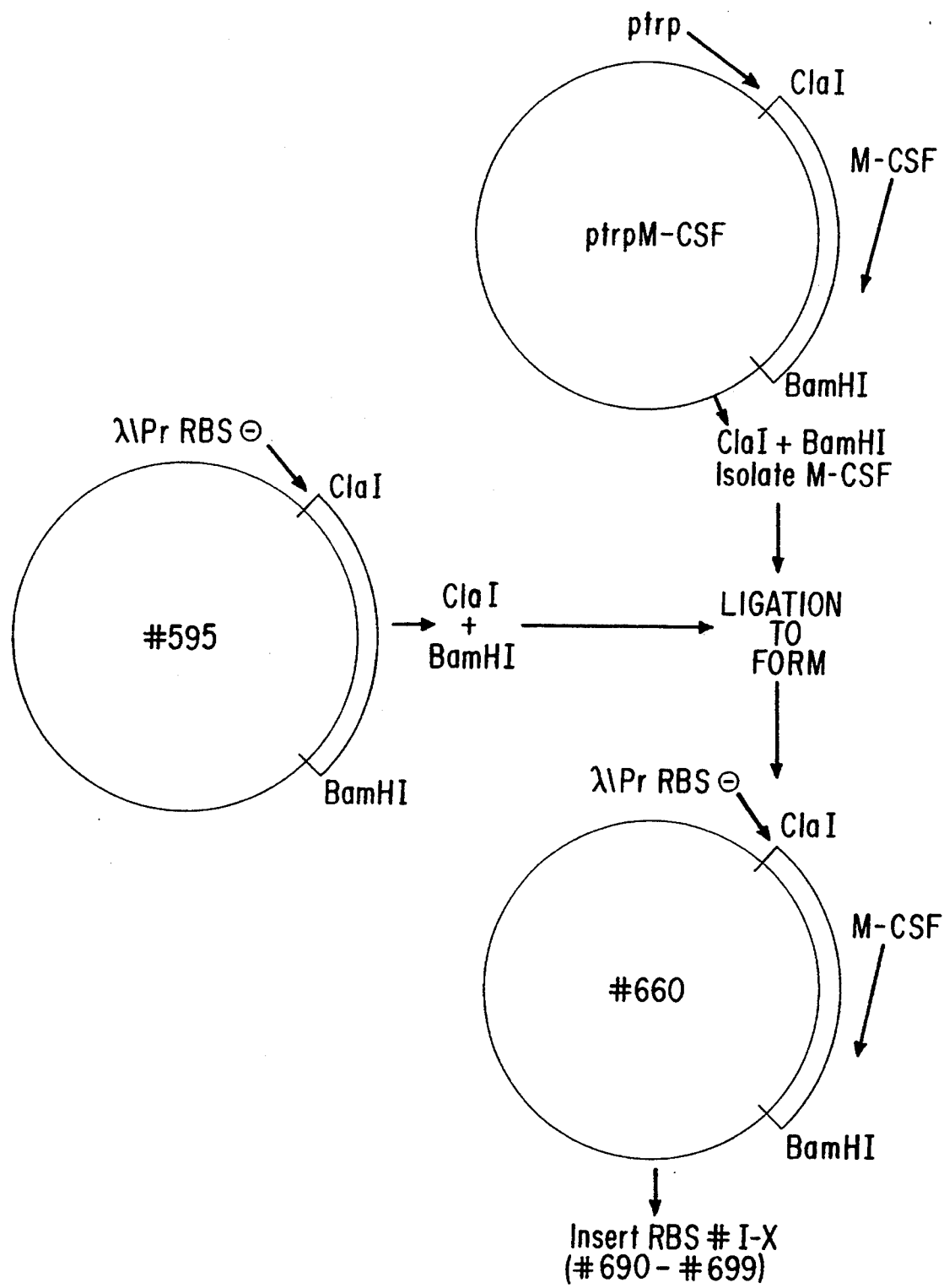
FIG. 4 schematically illustrates the synthesis of plasmid #660. This plasmid is analogous to plasmid #595, except that the IL-1$\beta$ sequences have been replaced by those coding for the truncated form of M-CSF. In 10 separate ligations, using the 5' untranslated leader sequences shown in Table 1, plasmids #690-699 were constructed. These plasmids are analogous to plasmid #660 except that each contains a 5' untranslated leader sequence with an RBS that allows for the synthesis of the protein of interest (M-CSF).

Plasmid ptrpM-CSF retains the coding region extending from the 35th amino acid (Val) of the precursor of M-CSF through the 185th amino acid (Thr) of the precursor of M-CSF (see FIG. 4; and European Patent Publication No. 261,592). The resulting mixture was then phenol extracted, and the DNA was ethanol precipitated and resuspended in 20 μl of water. The resulting digested DNA was electrophoresed on a 1.0% (w/v) agarose gel as described in Sharp, P. A. et al, *Biochem.*, 12:3055 (1973), so as to isolate a 475 bp fragment, containing sequences encoding the truncated M-CSF and an initiation (ATG) codon.

The 475 bp fragment was then ligated into an equal molar amount of plasmid #595, which had also been digested with ClaI and BamHI as described above (see FIG. 5).

Next, *E. coli* strain HB101 was transformed with the resulting plasmids as described in the BRL protocol for transforming HB101.

Recombinant plasmids were screened by randomly selecting 32 colonies generated by the transformation. More specifically, plasmid DNA was isolated as described by Maniatis, T. et al., *Molecular Cloning Manual*, Cold Spring Harbor, Laboratory, (1982). The resulting plasmid DNAs were screened by digesting each with the restriction endonuclease StuI. Only those plasmids having taken up the M-CSF insert isolated from ptrpM-CSF will cleave with StuI because the M-CSF insert, and not plasmid #595, contains a recognition site for this enzyme. The results were confirmed on 1.0% (w/v) agarose gels. In this manner, plasmid #660 was obtained (see FIG. 4).

Plasmid #660 contains all of the genetic signals required to synthesize M-CSF mRNA transcripts with the exception of the 5' untranslated leader sequences containing an RBS. Thus, 10 such sequences were synthesized to insert into plasmid #660 at the ClaI restriction site discussed above.

The 20 oligomers required to make the 10 desired sequences were synthesized on a Gene Assembler oligonucleotide synthesizer made by Pharmacia, S. A. All of the oligomers were synthesized and purified according to the manufacturer's specifications.

Purified oligomers were annealed in their appropriate pairs (see Table 1) by boiling 50 pMoles of each strand with its complementary partner for 5 min. in 100 μl of water. The 10 mixtures were then allowed to cool slowly to room temperature. Each annealed pair was then treated with polynucleotide kinase in order to add a 5' phosphate to each strand. The reaction mixture, using a standard protocol from Pharmacia, S. A., was as follows:

| Oligomer Mixture | 100 μl | (Table 1) |
|---|---|---|
| 10x Kinase buffer | 12.5 μl | |
| $^{32}$P gamma-ATP | 3.5 μl | (10 mCi/ml; 6000 Ci/mMol) |
| 10 mM ATP | 3.0 μl | |
| water | 4.0 μl | |
| Kinase | 2.0 μl | (Pharmacia, S.A. 10 units/ml) |
| | 125 μl | |

The reaction mixtures were kept at 37° C. for 30 min., heated to 65° C. for 5 min. and then purified over NACs ™ (BRL) using the manufacturer's specifications.

Plasmids #660 was prepared for the insertion of these oligomers by cleaving it with ClaI. More specifically, about 8.0 μg of plasmid #660 DNA was cleaved in 217 μl of water using buffer comprising 10 mM Tris (pH 7.5) and 10 mM MgCl$_2$, and using 50 units of ClaI in a total volume of 250 μl. The reaction was run for 2½ hours at 37° C. At this time, 30 μl of 10 x CAP buffer comprising 100 mM Tris (pH 8.0), 18 μl of water and 2.0 μl (8.0 units) of calf alkaline phosphatase (Boehringer Mannheim) were added. The reaction was allowed to continue for 30 min. at 37° C. The mixture was then heated to 65° C. for 5 min., phenol extracted and precipitated with ethanol as specified by the manufacturer. The DNA was then pelleted and resuspended in 20 μl of water.

Ten ligations were performed in which a 50–100 molar excess of oligomer to plasmid #660 was used. The mixtures were transformed into *E. coli* strain HB101 as discussed above. Recombinants were screened to identify those recombinant plasmids that had received one insert in the correct orientation. In this manner, plasmids #690–699 were obtained.

Plasmids #690–699 were tested for efficiency of expression of truncated M-CSF by inserting them individually into *E. coli* strain SG21058 obtained from Dr. Susan Gottesman, Laboratory of Molecular Biology, National Cancer Institute, Bethesda, Md., 20892, one of several hosts that allows the accumulation of truncated M-CSF. The different candidates were characterized by extracting mRNA from induced and uninduced cells as described in Example 1.

Total protein extracts from the resulting 10 transformed hosts from induced and uninduced cells were also assayed by examination on SDS-PAGE and Western blots as described in Example 1.

The only difference was that in each case M-CSF-specific probes were used. That is, an oligomer specific to M-CSF mRNA was used to detect the presence of M-CSF transcripts and an anti-M-CSF antibody was used to detect the presence of M-CSF in total protein extracts.

The results demonstrated that three constructs produced more truncated M-CSF than the others. These were plasmids #693, #696 and #699. (see Table 1). As with Example 1, the regulation of expression was tight, i.e., there was no detectable M-CSF prior to induction.

Microorganisms S-#660 (HB101), S-#693 (SG21058), S-#696 (SG21058) and S-#699 (SG21058) have been deposited at the American Type Culture Collection under ATCC Nos. 68061, 68062, 68063 and 68064, respectively.

III Fermentation

As discussed above, important parameters for growth are temperature, pH and oxygen transfer. Further, nutrition, as defined by the specific sources of carbon, nitrogen, phosphorus, sulfur and minerals is equally important.

The fermentation for the production of IL-1β in plasmid #599 (JM101) was carried out as follows:

Seed stocks were prepared by growing the above-described transformed microorganisms for 6 hours in standard Luria broth containing 100 μg/ml of ampicillin and 0.2% (w/v) glucose at 30° C. in a total volume of 50 ml. The resulting 50 ml mixture was then diluted in 250 ml of Luria broth containing 100 μg/ml of ampicillin and 0.2% (w/v) glucose at 30° C. for 3 hours or until the O.D. at $A_{600}$ was about 3 units/ml.

Thereafter, about 100 ml of the seed stock was diluted into a sterile solution containing 5.4 g of ammonium sulfate, 2.7 g of potassium phosphate, 0.9 g of potassium hydrogen phosphate, 12 mg of biotin, 0.025 ml of SAG Antifoam (Union Carbide) in 750 ml of water. Additionally, the following nutrients were added, in batch, as per the standard concentrations required for growth of *E. coli* used in the art: glucose, niocin, and Dawes trace elements consisting of zinc sulfate, iron chloride, manganese chloride, copper sulfate, cobalt chloride, boric acid, magnesium sulfate, calcium chloride, Na₂MoO₄ and thiamine (Wang, D. et al, *Fermentation and Enzyme Technology*, John Wiley & Sons (1979); and Demain, A. et al, *Biology of Industrial Microorganisms* (1985)).

Glucose was added at 1.0 to 2.0% (w/v) at the start and fed on demand to maintain a constant level of about 0.2% (w/v) once the initial supply was exhausted, with supplemental minerals and vitamins also added to maintain a constant level.

The pH was maintained at about 6.8 by the addition of phosphoric acid or sodium hydroxide.

Agitation was begun at 350 RPM and gradually increased to about 750 RPM throughout the run so as to maintain efficient aeration.

Dissolved oxygen levels were monitored and maintained at about 20% throughout the run by an increase of airflow and agitation rates.

Cell growth was monitored by O.D. measurements at $A_{600}$. When optimum cell concentrations were reached, i.e., 30 to 50 units/ml, the temperature was shifted from 30° C. to 42° C. for the induction of IL-1β expression. The induction period was then maintained for 8 to 10 hours and the cells were harvested by centrifugation at 6000 RPM for 45 min. at 4° C. and lysed by suspending the pellet in 100 ml of Tris buffer (pH 7.0). The cells were then passed through a French pressure cell at 18,000 PSI to break open the cells and IL-1β was purified as described by Kikumoto, Y. et al, *Biochem. Biophys. Res.*, 147:315–321 (1987).

The truncated M-CSF can be purified as described in Japanese Patent Application Ser. No. 1-24663 and European Patent Publication No. 261,592.

The table below provides the sequences of ten 5' untranslated leader sequences, containing an RBS, and designed to be inserted into plasmid #595, wherein the gene located 3' of the ClaI site can be any gene of choice.

| RBS # | SOURCE | SEQUENCE | PLASMID # |
| --- | --- | --- | --- |
| I | *E. coli* lac Y | CGTATTACGCGTAAGGAAATCCAT ATAATGCGCATTCCTTTAGGTAGC | 690 |
| II | *E. coli* trp D | CGAATCTAGATGCACAGGAGACTTTCTAT TTAGATCTACGTGTCCTCTGAAAGATAGC | 691 |
| III | φX174 E | CGTCGACGCGTTGAGGCTTGCGTTTAT AGCTGCGCAACTCCGAACGCAAATAGC | 692 |
| IV | *E.* Rec coli Rec A | CGAATACGCGTCATGACAGGAGTAAAAT TTATGCGCAGTACTGTCCTCATTTTAGC | 693 |
| V | Novel | CGTATGTCTGAGAATATGGAGGAAATTAT ATACAGACTCTTATACCTCCTTTAATAGC | 694 |
| VI | *E. coli* lac Y Modified | CGTTTAACGCGTTAAAGGAAGGATCAT AAATTGCGCAATTTCCTTCCTAGTAGC | 695 |
| VII | *E. coli* trp D Modified | CGAAATCTAGATGCAAAGGAGATTTAT TTTAGATCAACGTTTCCTCTAAATAGC | 696 |
| VIII | φX174 E Modified | CGTCGACGCGTTGAGGCTTAAATTTAT AGCTGCGCAACTCCGAATTTAAATAGC | 697 |
| IX | *E. coli* Rec A Modified | CGAATACGCGTCATTATAGGATTAAT TTATGCGCAGTAATATCCTAATTAGC | 698 |
| X | Novel Modified | CGTATGTCTGAGAATTTGGAGGTTTAAAT ATACAGACTCTTAAACCTCCAAATTTAGC | 699 |

While the invention has been described in detail and with reference to specific embodiments thereof, it will be apparent to one skilled in the art that various changes and modifications can be made therein without departing from the spirit and scope thereof.

We claim:

1. A gene regulation cassette comprising native lambda $P_R$ operator/promoter, two base pairs 3' of the start of transcription of said operator/promoter and a restriction site encompassing or adjacent to said two base pairs, wherein said cassette has the following DNA sequence:

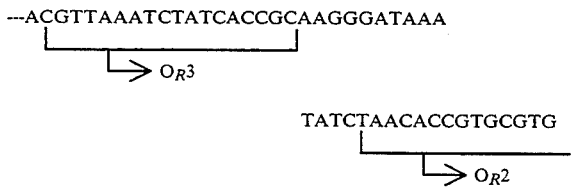

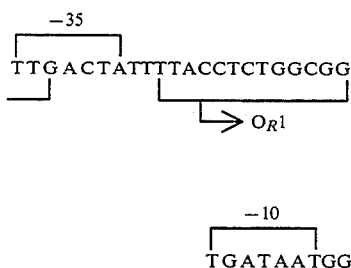

2. An expression vector comprising the gene regulation cassette of claim 1 having the DNA sequence:

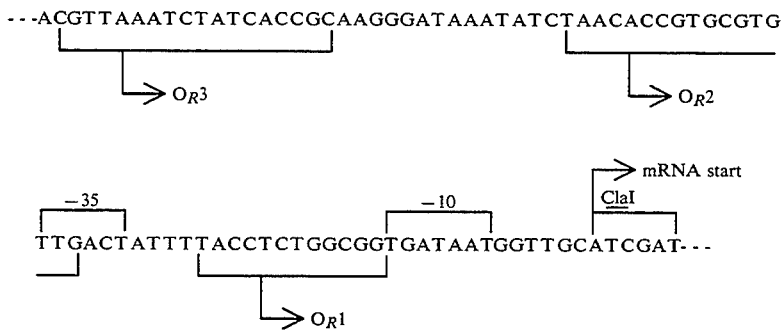

operably linked to a gene that encodes a protein.

3. The expression vector as claimed in claim 2, wherein said expression vector is plasmid #595 or plasmid #660.

4. The expression vector of claim 2, wherein said heterologous gene encodes IL-1β or M-CSF.

5. A microorganism comprising the expression vector of claim 2, wherein said expression vector comprises a gene regulation cassette having the DNA sequence:

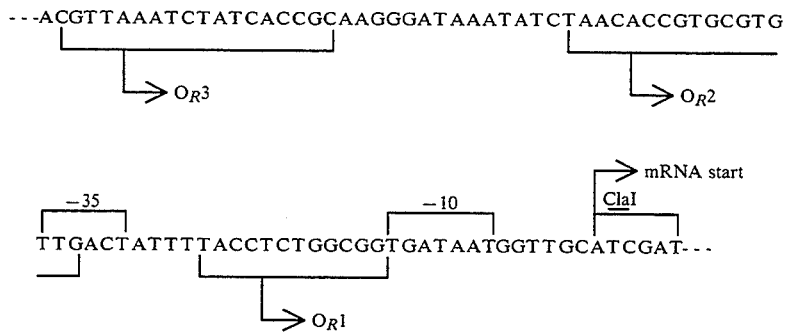

operably linked to a gene that encodes a protein.

6. The microorganism as claimed in claim 5, wherein said expression vector is plasmid #595 or plasmid #660.

7. The microorganism as claimed in claim 5, wherein said microorganism has the identifying characteristics of S-#595 (HB101) (ATCC No. 67755) or S-#660 (HB101) (ATCC No. 68061).

8. The microorganism of claim 5, wherein said heterologous gene encodes IL-1β or M-CSF.

9. A gene regulation cassette comprising native lambda $P_R$ operator/promoter fused to a 5' untranslated sequence of the tryptophan leader including a ribosome binding site.

10. The gene regulation cassette of claim 9, having the following DNA sequence:

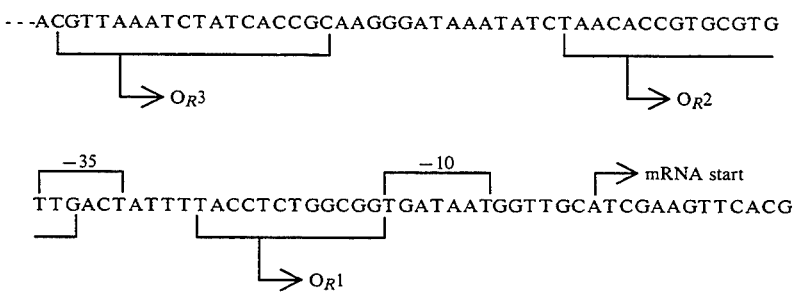

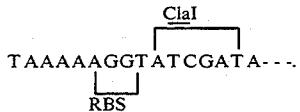

11. An expression vector, comprising:
(A) a gene regulation cassette consisting essentially of native lambda $P_R$ operator/promoter fused to a 5' untranslated sequence of a tryptophan leader including a ribosome binding site; wherein said cassette is operably linked to
(B) a gene that encodes a protein.

12. The expression vector as claimed in claim 11, wherein said gene regulation cassette has the following DNA sequence:

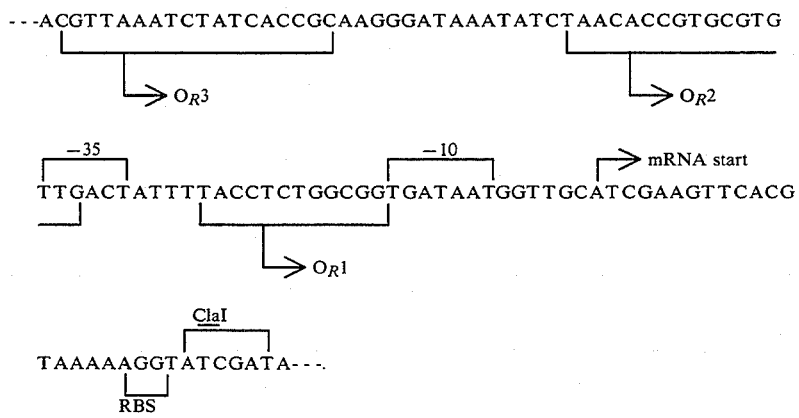

13. The expression vector as claimed in claim 11, wherein a terminator is added 3' to the gene that encodes a protein.

14. The expression vector as claimed in claim 11, wherein said vector additionally comprises:
(C) the lambda cI857 repressor gene; and
wherein said vector is capable of expressing the lambda cI857 repressor.

15. The expression vector as claimed in claim 11, wherein said expression vector is selected from the group consisting of plasmid #599, plasmid #693, plasmid #696 and plasmid #699.

16. The expression vector of claim 11, wherein said heterologous gene encodes IL-1β or M-CSF.

17. A microorganism, comprising an expression vector, said expression vector comprising:
(A) a gene regulation cassette consisting essentially of native lambda $P_R$ operator/promoter fused to a 5' untranslated sequence of a tryptophan leader including a ribosome binding site; wherein said cassette is operably linked to
(B) a gene that encodes a protein.

18. The microorganism as claimed in claim 17, wherein said gene regulation cassette has the following DNA sequence:

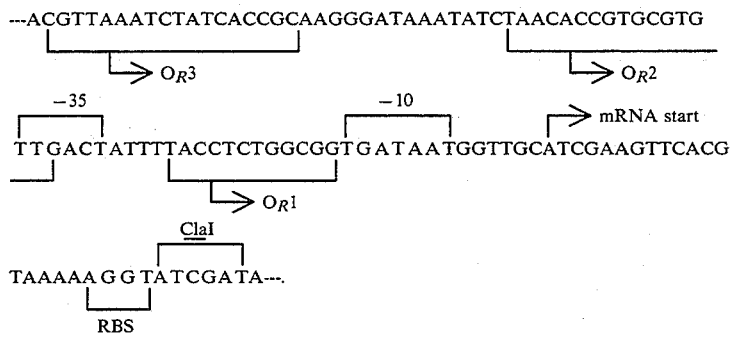

19. The microorganism as claimed in claim 17, wherein a terminator is added 3' to the gene that encodes a protein.

20. The expression vector as claimed in claim 17, wherein said vector additionally comprises:
(C) the lambda cI857 repressor gene; and
wherein said vector is capable of expressing the lambda cI857 repressor.

21. The microorganism as claimed in claim 17, wherein said expression vector is selected from the group consisting of plasmid #599, plasmid #693, plasmid #696 and plasmid #699.

22. The microorganism as claimed in claim 17, wherein said microorganism has the identifying characteristics of S-#599 (JM101) (ATCC No. 67756), S-#693 (SG21058) (ATCC No. 68062), S-#696 (SG21058) (ATCC No. 68063) or S-#699 (SG21058) (ATCC No. 68064).

23. The microorganism of claim 17, wherein said heterologous gene encodes IL-1β or M-CSF.

* * * * *